United States Patent
Rickert et al.

(10) Patent No.: US 12,076,567 B2
(45) Date of Patent: Sep. 3, 2024

(54) SYSTEM AND METHOD FOR NEUROSTIMULATION

(71) Applicant: CorTec GmbH, Freiburg (DE)

(72) Inventors: Jörn Rickert, Freiburg (DE); Christian Stolle, Freiburg (DE); Martin Schüttler, Emmendingen (DE)

(73) Assignee: CorTec GmbH, Freiburg (DE)

( * ) Notice: Subject to any disclaimer, the term of this patent is extended or adjusted under 35 U.S.C. 154(b) by 0 days.

(21) Appl. No.: 18/092,718

(22) Filed: Jan. 3, 2023

(65) Prior Publication Data

US 2023/0149715 A1    May 18, 2023

Related U.S. Application Data

(63) Continuation of application No. 15/829,241, filed on Dec. 1, 2017, now abandoned, which is a continuation
(Continued)

(30) Foreign Application Priority Data

Jun. 3, 2015   (DE) .................. 10 2015 108 861.4

(51) Int. Cl.
*A61N 1/36*       (2006.01)
*A61B 5/00*       (2006.01)
(Continued)

(52) U.S. Cl.
CPC ............ *A61N 1/36139* (2013.01); *A61B 5/24* (2021.01); *A61B 5/4082* (2013.01);
(Continued)

(58) Field of Classification Search
CPC ....... A61B 5/24; A61B 5/4082; A61B 5/4836; A61N 1/36067; A61N 1/36139;
(Continued)

(56) References Cited

U.S. PATENT DOCUMENTS

| | | |
|---|---|---|
| 2005/0102006 A1 | 5/2005 | Whitehurst et al. |
| 2007/0213786 A1 | 9/2007 | Sackellares et al. |

(Continued)

FOREIGN PATENT DOCUMENTS

| | | |
|---|---|---|
| CN | 102905757 A | 1/2013 |
| CN | 102934142 A | 2/2013 |

(Continued)

OTHER PUBLICATIONS

International Search Report issued for corresponding International patent Application No. PCT/EP2016/062668 mailed on Aug. 29, 2016.
(Continued)

*Primary Examiner* — Jon Eric C Morales
(74) *Attorney, Agent, or Firm* — Myers Wolin, LLC (57) ABSTRACT

A brain stimulation method and system are provided, wherein neuronal signals of a patient are continuously sensed by at least one sensor device and based on the sensed signals, stimulation signals are applied to the patient by at least one stimulation device, wherein the sensed signals are transmitted to a body-external, portable processing device wherein the sensed signals are evaluated, and based on the evaluated signals stimulation control signals are generated and transmitted to the stimulation device where based on the stimulation control signals the stimulation signals are generated.

11 Claims, 6 Drawing Sheets

Related U.S. Application Data of application No. PCT/EP2016/062668, filed on Jun. 3, 2016.

(51) Int. Cl.
*A61B 5/24* (2021.01)
*A61N 1/372* (2006.01)
*A61N 1/375* (2006.01)
*G16H 10/60* (2018.01)
*G16H 40/63* (2018.01)

(52) U.S. Cl.
CPC ........ *A61B 5/4836* (2013.01); *A61N 1/37217* (2013.01); *A61N 1/37282* (2013.01); *A61N 1/36067* (2013.01); *A61N 1/37247* (2013.01); *A61N 1/37264* (2013.01); *A61N 1/37514* (2017.08); *G16H 10/60* (2018.01); *G16H 40/63* (2018.01)

(58) Field of Classification Search
CPC ............ A61N 1/37217; A61N 1/37247; A61N 1/37264; A61N 1/37282; A61N 1/37514; G16H 10/60; G16H 40/63
See application file for complete search history.

(56) References Cited

U.S. PATENT DOCUMENTS

| | | | | |
|---|---|---|---|---|
| 2008/0114415 | A1* | 5/2008 | Dai | A61N 1/378 607/54 |
| 2010/0049281 | A1* | 2/2010 | Libbus | A61B 5/24 600/300 |
| 2014/0180361 | A1* | 6/2014 | Burdick | A61N 1/36107 607/48 |
| 2014/0243926 | A1 | 8/2014 | Carcieri | |
| 2018/0078770 | A1* | 3/2018 | Rickert | A61N 1/36139 |

FOREIGN PATENT DOCUMENTS

| | | | |
|---|---|---|---|
| CN | 103608069 | A | 2/2014 |
| CN | 103796715 | A | 5/2014 |
| CN | 104096313 | A | 10/2014 |
| CN | 104225790 | A | 12/2014 |
| CN | 104363956 | A | 2/2015 |
| DE | 102007003799 | A1 | 7/2008 |
| WO | 2009129478 | A2 | 10/2009 |
| WO | 2010109448 | A1 | 9/2010 |
| WO | 2012129574 | A2 | 9/2012 |

OTHER PUBLICATIONS

German Examination Report, dated Mar. 2, 2016, for corresponding German Application No. 10 2015 108 861.4 with an English translation.

Communication pursuant to Article 94(3) EPC issued by the European Patent Office for corresponding European Patent Application No. 16 726 881.2, dated Feb. 26, 2021.

The Third Office Action issued by the State Intellectual Property Office of People's Republic of China for corresponding Application No. 2016800323236, mailed on Sep. 17, 2021, with English translation attached.

Non-Final Office Action issued by the United States Patent and Trademark Office for corresponding U.S. Appl. No. 15/829,241, electronically delivered on Jun. 1, 2018.

Final Office Action issued by the United States Patent and Trademark Office for corresponding U.S. Appl. No. 15/829,241, electronically delivered on Jan. 22, 2019.

Non-Final Office Action issued by the United States Patent and Trademark Office for corresponding U.S. Appl. No. 15/829,241, electronically delivered on Aug. 7, 2019.

Final Office Action issued by the United States Patent and Trademark Office for corresponding U.S. Appl. No. 15/829,241, electronically delivered on Apr. 20, 2020.

Non-Final Office Action issued by the United States Patent and Trademark Office for corresponding U.S. Appl. No. 15/829,241, electronically delivered on Oct. 26, 2020.

Final Office Action issued by the United States Patent and Trademark Office for corresponding U.S. Appl. No. 15/829,241, electronically delivered on Apr. 19, 2021.

First Office Action with search report issued by the Chinese Patent Office for Chinese Patent Application No. 201680032323.6, dated Aug. 17, 2020.

* cited by examiner

SYSTEM AND METHOD FOR NEUROSTIMULATION

CROSS REFERENCE TO RELATED APPLICATIONS

This application is a continuation of U.S. patent application Ser. No. 15/829,241, filed on Dec. 1, 2017, which is a continuation of International Application No. PCT/EP2016/062668, filed on Jun. 3, 2016, which claims priority to German Application No. 10 2015 108 861.4, filed Jun. 3, 2015, the contents of each of which are incorporated by reference herein.

TECHNICAL FIELD

The present invention relates to a system and a method for neurostimulation, and in particular to a closed-loop neurostimulation method and system.

BACKGROUND

Current neurostimulation systems work as follows: A "brain pacemaker" contains implantable electrodes that are in contact with the brain/nervous system and a small battery-operated pulse generator, implanted under the skin in the upper chest.

The pulse generator emits a continuous series of electrical pulses, usually powered by a battery within the pulse generator, that are transmitted via cables and the implantable electrodes to the brain/nervous system (open-loop system).

The newest systems on the market adapt their stimulation based on measurements from implanted sensors—which can be either the same electrodes that are used for stimulation, additional electrodes, or other sensors integrated into the pulse generator. On the basis of the information from these sensors, the pulse generator performs simple, usually linear, signal processing leading to an adjustment of the stimulation, affecting either the timing of stimulation onset or other stimulation parameters.

In Parkinson's Disease (PD), for example, the standard open-loop treatment reduces the symptoms of the disease, such as slowness of movement, stiffness and tremor, by up to 70%. However, it also produces a number of side effects that can be so severe that neurostimulation, and in particular, deep brain stimulation (DBS) treatment has to be terminated (e.g., disturbances in impulse control, personality changes, or speech problems). Also, some deficits are insufficiently treated by DBS or even become worse. An example is freezing of gait (FOG)—a gait disturbance consisting of sudden interruptions in walking. This disturbance frequently occurs in PD patients. FOG episodes can be very disruptive for patients, can lead to falls and injury and has a considerable negative impact on the quality of life. Open-loop DBS has very disappointing effects on these gait disturbances. Often, there is no improvement of FOG by open-loop DBS at all, or sometimes even a worsening of freezing. Actually, gait and balance problems and freezing all tend to progress and become resistant to medications and to DBS. In addition, motor deficits of Parkinson's patients vary over time.

Recent research suggests that neurostimulation, in particular DBS treatment, can be improved by making the stimulation adaptive and taking the patient's current neuronal state into account. A few preclinical and clinical studies have shown that adaptive stimulation is clinically effective and superior to conventional continuous stimulation. Concerning FOG, there are attempts to detect FOG on the basis of neuronal signatures recorded from implanted electrodes. Once detected, the FOG could be treated by an adjustment of brain stimulation.

There is evidence that adaptive neurostimulation, in particular DBS can also be useful for other neurological and psychiatric diseases, e.g. epilepsy.

Adaptive DBS approaches need to be able to assess the moment-to-moment physiological status of the patient and identify the momentary need for stimulation.

SUMMARY

It is an object of the present invention to provide systems and methods which alleviate at least partially these problems. This object may be addressed by the systems and methods and computer-readable storage media according to the claims.

Thus, to improve neurostimulation treatment, the present disclosure suggests neurostimulation systems and methods, in particular closed-loop neurostimulation systems and methods that are able to combine several features in a single system.

Neuronal activity and/or states are sampled continuously, by using sensors that capture electrophysiological activity. Such sensors, in principle, can be invasive or non-invasive, and can measure central nervous or peripheral nervous signals and/or concentrations of molecules. For measuring nervous signals, the sensors need to be invasive.

Sensors are provided that measure other data with relevance to the clinical state of the patient, e.g., those that measure movement or acceleration of body parts (inertial measurement units—IMUs), video signals of the patients, measurement of concentrations of molecules in air or body fluids outside of the brain, or other physical sensors. These sensors are usually body external sensors.

Continuous analysis of incoming data can be performed, memory capacity (advantageously relying on databases or cloud solutions) is provided, and evaluation in terms of graduated variables in addition to classification into fixed categories and online learning of classification parameters is provided.

The continuous data analysis enables new strategies such as computation of stimulation on demand. Generally, stimulation demand $S(t1)$, i.e., the control signals, at time point $t1$ is determined on the basis of input from N sensors, and, therefore, can be computed as $S(t1)=f(sensor1(t1), sensor2(t1), \ldots sensorN(t1))$.

For many sensors, not only the information at one point in time, $t1$, is important, but, rather, from a number of previous points in time, $t-xi$. Thus, physically, the system needs a memory to store data from the sensors.

The stimulation demand S at time point $t1$ with input from N sensors, therefore, can be computed as $S(t1)=f(sensor1(t1,t1-x1,t1-x2, \ldots ,t1-xn), sensor2(t1,t1-y1, t1-y2, \ldots ,t1-yn), \ldots , sensorN( \ldots ))$.

Moreover, in contrast to existing closed-loop/simple adaptive systems, here, stimulation parameters vary gradually between values of 0 and maximal values in frequency and amplitude instead of changes between discrete, predetermined states.

In another embodiment, the demand of stimulation could be computed by a sensor in form of a multi-channel (>15 channels) grid-electrode implanted on the surface of motor areas of the cortex. A preferred signal of the sensor then being the amplitude of oscillations in a frequency range between 20 and 30 Hertz, computed as the average amplitude every 100 to 500 ms relative to a baseline amplitude (i.e. average across several hours preferably during rest).

A further strategy based on the continuous data analysis is an adaptive algorithm strategy. The brain adapts to the stimulation or changes through time, which is why the stimulation demands change. The function f itself, therefore, is then a function dependent on time, i.e., is adapted over time.

The adaptation of the brain is measured by the implanted sensors. In a preferred embodiment of the invention, the stimulation-induced neural activities recorded 1-100 ms after the stimulation are used as a measure to determine the effectiveness of the stimulation. I.e., if the stimulation-induced neuronal activities decrease, the stimulation parameters have to be changed, first, preferably, by changing stimulation frequency and/or pattern, otherwise by increasing stimulation intensity.

Stimulation-induced responses can be determined by standard methods of determining system responses to stimuli as described in systems theory (i.e. cross correlation, reverse correlation).

Adaptation of the function f takes place by varying the parameters of the function f. Usually, this is done by changing the weights of the function f with respect to the different sensors.

In addition, the function f itself can be updated from time to time depending on new knowledge of the best treatments and or input from the database.

To implement the new features described above, the body-external, portable processing device provides the following features:

Realizing such complex computations requires a lot of computational power. This cannot be easily realized in implanted systems. Therefore, the patient's body-external, portable processing device performs the computations and transfers the resulting control signals to the implantable control unit.

To store the recordings of all sensors over significant periods of time, large memory space is required—likely exceeding the storage capacity of implantable control units, thus, the memory is provided in the body-external, portable processing unit.

If the data collected over a longer period of time exceed the capacity of the memory of the body-external, portable processing device, and for reasons of backup and/or external analysis of the data, the data stored in the portable processing unit may be transferred to a patient external storage home-device or directly uploaded to an external database via internet.

BRIEF DESCRIPTION OF THE DRAWINGS

The invention is described by reference to the drawing, in which.

DETAILED DESCRIPTION

Figure 1:
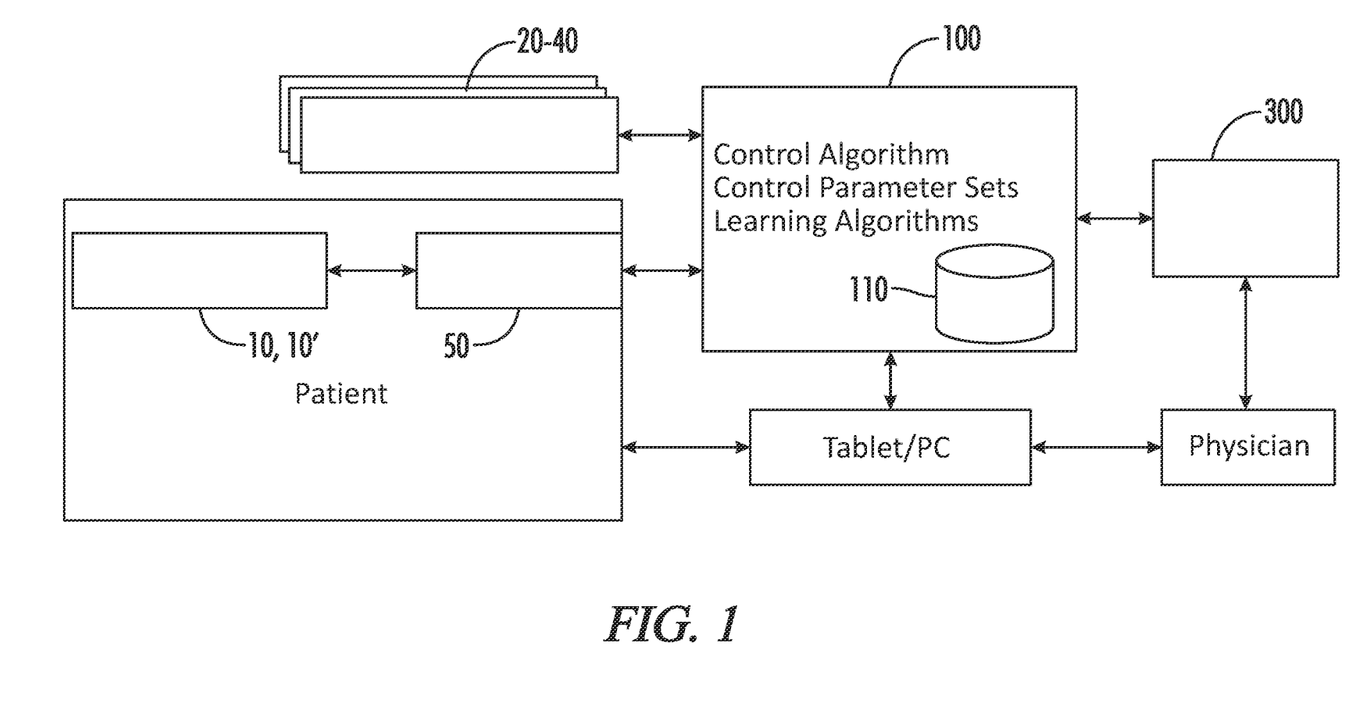
FIG. 1 is an overview scheme illustrating an exemplary realization at system level according to the invention.

One realization of the invention at system level is illustrated in FIG. 1. The neural implant 10, 10' as well as external sensors 20-40 provide their data to a body-external, portable processing device 100. Based on this data, stimulation demand S(ti) is computed, and S is used for updating the stimulation function, sent to the neural implant 10'. Therefore, the body-external, portable processing device 100 acts as a local controller, providing "set points" based on the sensor feedback and a set of control parameters. This set of parameters may include, e.g., sensor settings, pattern recognition algorithm parameters and thresholds, neural network weights.

The body-external, portable processing device 100 stores the sensor data S and the control parameters in a local database 110, 115 on a flash drive to prevent data loss on power failures. Each data set is annotated with the current system time. The recorded data can be reviewed and analyzed via a tablet or PC. In addition, the data can be synchronized via a network connection into a central database 300. A time base conversion and time shift correction may be required. Either the patient itself or the physician can access the local data sets to monitor the effectiveness of the treatment or to update control parameters, e.g., intensity of the stimulation signal.

As security and patient safety measures, the software on the body-external, portable processing device 100 may restrict the control parameter space, depending on the role of the person connected to the device. If the physician is providing the updates, the parameter space is less restricted than if the patient itself is changing the parameters. The physician may define the patient's parameter subspace as well as change the control algorithm if another algorithm is more suitable for the patient's condition. In addition, the physician may define different control parameter sets, which may be selected by the patient depending on different tasks he wants to archive (e.g. sleeping may require a different set of parameters than walking). The physician may use the services of the central database for offline analysis of the patient's data sets. This may incorporate computational complex offline algorithms such as neural network algorithms (e.g. Back Propagation, etc.) to derive the best fit set of control parameters according to the current patient needs.

The body-external, portable processing 100 device itself may run online or offline learning algorithms for adjusting the stimulation parameters. This is achieved by continuously providing each data set sensed respectively by the sensors 10, and sensors 20-40 (if present) and control algorithm output as input of the learning algorithm, i.e., in a closed-loop manner. The output can change control parameters "on the fly" e.g., applied to a fuzzy logic controller with an artificial neural network for online control parameter learning. The advantage of this online learning approach is that it can handle daily fluctuations of the patient's condition.

Moreover, the stimulation function f may be adapted with respect to safety issues of the patient or her/his environment. Hereto, one or more further body-external sensors 20-40, such as GPS or other geo-position sensors may be provided which are adapted to provide local and/or movement data to the body-external, portable processing device 100. Then, if the patient is detected to move with speed which is faster than a predetermined level, and the patient is detected to run a car, the stimulation may be increased directly to a more effective level.

Moreover, patient's pulse rate and/or transpiration, and/or tension may be sensed by appropriate sensors 20-40. Based on the sensed data, the stimulation function f may be adapted.

Calibration of the system can be achieved by recording the system's impulse response: Approximated by recording the neural activities/sensor activities in response to the strongest possible and medically save single pulse stimulation/actuator activity applied. As the stimulation pulse for safety reasons is limited in strength to the maximal stimulation (voltage or current) allowed, this characterization is carried out repeatedly, typically 10-25 times, and the results are averaged until only minor differences occur and statistical significance of the model is reached.

The model of the system generated by this characterization, i.e., the system's impulse response, can be used to predict sensor activities in response to certain stimulation/actuator patterns. This can be used twofold: 1. to define the stimulation/actuator activities that produce sensor activities indicative for a desired patient state, for example low oscillations in the beta-range in certain brain regions, i.e., the motor cortex or in the nucleus subthalamicus, and 2. to prevent stimulation parameters that achieve undesired neural activities/brain states, for example activity that leads to increased oscillations in the beta range in certain brain regions, activity that might lead to seizures, invoke uncontrolled movements.

If the system is designed as an open-loop system, the stimulation control unit may be designed as an implanted pulse generator having stimulation parameters which are within a range defined by the clinician. Then, the patient performs exercises on an electronic input device such as tablet PC or the portable processing unit on a regular basis, e.g., drawing a circle or handwriting. The exercises performed by the patient are evaluated, and based on the evaluation, the stimulation signals (within the range) are determined. Moreover, symptoms of diseases may be evaluated. All the data and evaluations may be transferred to an external data base. To reduce risks of cables (between electrodes and stimulator) breaking (due to many movements of the neck), the stimulator control unit is preferably implanted directly in the head. This is especially important if advanced systems with high number of channels/electrode contacts (going along with many wires that cannot be coiled because then the cable gets too thick) are used. Thus, a flat implant sitting in skull is required to mitigate this risk. This gets even more important if implants without connectors between cables and stimulator are used, as then no component can be explanted without removing the whole system.

In the following an exemplary system with respect to the sensor data acquisition and processing is described in further detail wherein the system and method can be implemented.

Figure 2:
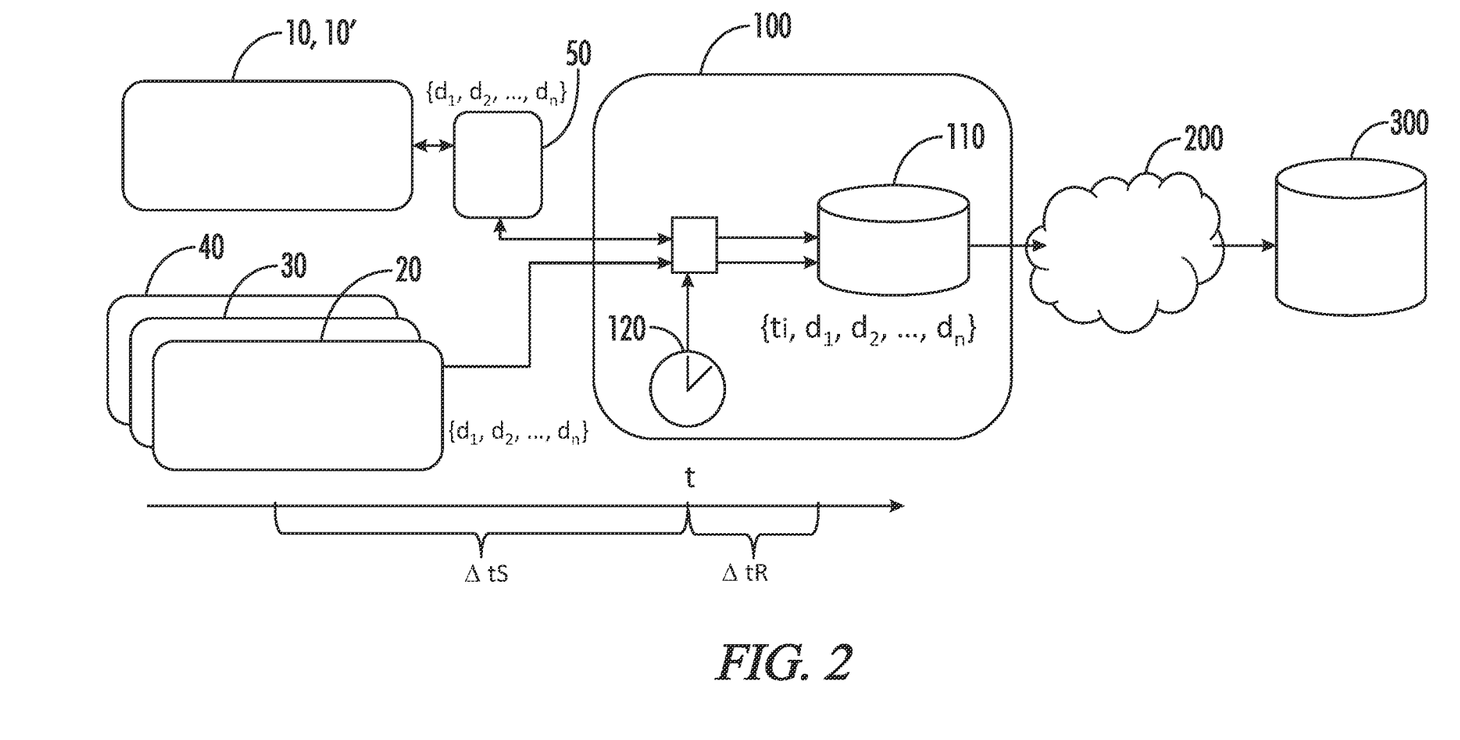
FIG. 2 is a scheme illustrating the data acquisition flow according to an embodiment of the invention.

The embodiment of FIG. 2 is a configuration where data originating from a patient is sensed, recorded, and further processed. As shown in FIG. 2, one or more neural electrode implants 10 are connected to an implant control unit 50, which in turn is coupled with a body-external, portable-external, portable processing device 100. Further sensors 20-40 may be present which are also coupled with the body-external, portable processing device 100. The neural implant(s) 10 and the further sensors 20-40 sense, e.g., neural signals, and other parameters from inside or outside human body. The sensed signals are converted into data streams and transmitted to the body-external, portable processing device 100 for further processing. Implant control unit 50 is arranged in the data flow between the neural implant(s) 10 (and the further sensors 20-40) and the body-external, portable processing device 100 for reasons of space and accessibility. A neural implant 10 will in general not offer sufficient space for control electronics of the neural implant(s) 10 and for communication electronics to the outside of the human body.

More precisely, body-external, portable processing device 100 comprises a temporal storage 110 for at least temporal recording data streams $\{d_1, d_2, \ldots, d_n\}$, a time reference 120 for generating time stamps t and processing means for associating the data streams $\{d_1, d_2, \ldots, d_n\}$ with the time stamps t. That is, each of the data streams $\{d_1, d_2, \ldots, d_n\}$ representing the signals is recorded along with a time stamp information which is generated just at the time of actually recording the respective data stream.

Thus, the implant control unit 50 and the sensors 20-40 relay their signals in the form of data streams $\{d_1, d_2, \ldots, d_n\}$ to the body-external, portable processing device 100. The body-external, portable processing device 100 is a body-external device that can be carried by the patient. It comprises the time reference 120 which is used to generate sufficiently precise time stamps t (e.g., with precision in the order of one or more microseconds) and a temporal storage 110 (e.g., a sufficiently large hard disc or flash disc). When a data stream arrives at the body-external, portable processing device 100, a time stamp t is generated and assigned to this data stream and both are stored in the temporal storage 110. When a connection via a data transportation medium 200 (e.g., internet or local area network) to a database 300 is possible, the data from the temporal storage 110 (i.e., the data streams along with their time stamps) is transferred to the database 300. For the database 300, there are several configurations possible. E.g., the database can be a database server in a server farm/cloud or a computer at the patient's home.

The body-external, portable processing device 100 may be a PDA, a smartphone or the like.

Depending on the nature of the signals (or parameters) to be sensed, neural electrode implant(s) 10 and sensors 20-40 can be: For invasive physiological parameters, electrodes for recording electrical activity (voltage, current) from the brain or individual nerves, sensors for sensing of electrochemical gradients in order to identify concentrations of biomolecules, sensors for pH or blood glucose. For noninvasive physiological parameters, EMG, heart rate, skin conductivity, body movements (accelerometers), blood pressure. Exemplary other non-physiological parameters to be sensed by sensors outside human body 20-40 are GPS position, environment parameters such as temperature, noise/sound (in Decibels), lightning level, weather. Some or all of the sensors 20-40 may be integrated within the body-external, portable processing device 100.

Neural electrode implant 10 may be a combined sensor and stimulation implant, i.e., it may function as a device for sensing neuronal signals, and as a device for applying stimulation impulses (signals) to the neuronal system.

Sensing neuronal activity and applying neuronal impulses may also be performed individually by separate neural electrode implants. Then, at least two neural electrode implants are provided, one implant 10 for sensing neuronal activity, and one implant 10' for applying stimulation impulses (signals).

Invasive actuators can be: Electrodes for electrical stimulation of the brain or individual nerves, actuators for applying medication, noninvasive actuator can be: Hand-/arm or speech prostheses, warning sensors sending alarms to hospitals/physician or to the patient himself.

The time reference 120 can be a radio-controlled clock, a timeserver regularly updating system time running on electronics, GPS, network time protocol (interne used by PCs/ electronics to update their time automatically), and other means which deliver exact coordinated universal time information (UTC). The precision should be preferably in an order of magnitude of milliseconds as mentioned above, and more preferably in an order of 2-4 ms, in particular cases it should be 1 ms. This corresponds to the order of magnitude of the sampling rate of the neural signals.

Taking as the time stamp t the point in time of storing the respective data stream in the temporal storage 110 of the body-external, portable processing device 100, this may not be sufficiently exact for the purpose of synchronizing the data streams with data streams captured with other sensors, and/or for triggering stimulation pulses. The reason for that is that there may be substantial delays between actually sensing the signals by the implant 10, or by the other sensors 20-40, and storing them in the temporal storage 110 of the body-external, portable processing device 100, where the time stamp t is generated. This is in particular true for neuronal signals, which are extremely short and may have spectral portions and/or frequencies in the order of magnitude of some kHz up to some MHz.

Thus, the exact time synchronization may take into account for each neural implant 10, sensor devices 20-40, and processing device 100, the delay $\Delta t_S$ between the point in time of actual sensing the signal by the neural implant 10, sensor devices 20-40, and the point in time t when a time stamp was generated and associated with the data stream representing the sensed signal, i.e., the point in time when the data stream is actually going to be recorded by the processing device 100. In general, for each sensor 10, 20-40, the respective delays $\Delta t_S$ will exhibit a respective predefined probability distribution. From the knowledge of the respective probability distribution, the delay $\Delta t_S$ for a particular sensor can be derived. For example, a sensor device 10, 20-40 which exhibits a Gaussian distribution for its delay $\Delta t_S$ can be modeled by its mean delay and the variance of the delay. Given these parameters, the most likely point in time of the event occurrence (represented by the sensed signal) can be calculated from the stored time stamp t.

Further, the delay $\Delta t_R$ of the recording means of the body-external, portable processing device 100 itself may be taken into account (if there is any). Then, the delay $\Delta t_S$ between sensing the signal (representing the event) and recording the data stream as well as the delay $\Delta t_R$ of the recording means of the time-processing device 100 itself is taken into account, i.e., by directly subtracting the difference in the average delay between time-processing device 100 and sensor signal from the stored time stamp t associated with the data stream: $t'=t-(\Delta t_S+\Delta t_R)$. Other computations of the delays $\Delta t_S$, $\Delta t_R$ may be performed if the time reference points and/or the signs of the delays are different.

As a minimum information, average delays should be known. All information about the delays of particular implants 10, sensors 20-40, implantable control unit 50, and processing devices 100, respectively, is preferably stored in a product specification database 400, which may preferably be external to the body-external processing device 100 and database 300.

The data streams thus temporally aligned (i.e., synchronized with each other) may be used for adaptation and update of therapeutic parameters: First of all, the therapeutic parameters of the neural implant 10 and its implantable control unit 50 can be updated based on the data stored in the database 300: Analysis of the database will send via the data transportation medium 200 (same way backwards as the data upload described above) an update to the actuators (implants) and sensors 10-40 and the implant control unit 50 where the algorithm for the computation of actuator activity based on the recorded sensor activity will be updated. For example, neural activity in particular is known to change or adapt over time because of learning, habituation and other factors of neuronal plasticity. To take this into account, therapeutic parameters need to be adapted likewise over time.

In another mode, this update runs via the patient's private network device 200, where the patient can control the update manually (i.e. for testing etc.). Every change to the parameter set of a sensor 20-40 or an actuator (implant) 10 is also stored in the database 300 and is annotated with a respective time stamp. This way, changes to sensors 20-40 and actuators 10 are also traceable.

Moreover, the data stored in the database 300 can be used by physicians for diagnostics. In one version, the data of a certain set of parameters in a time-window of interest can be made available to the physician.

In an advanced version, diagnostic data acquired and recorded by a physician with his own technical equipment, clinical staff, or by the patient himself, is labeled with a time stamp t too, and uploaded to and stored in the database 300, whereby the time stamps are corrected as described above. Conversely, the physician may use the time-stamped data he recorded with his equipment directly, without uploading to the database 300, in combination with the data recorded by the body-external, portable recording unit 100 and uploaded to the database 300.

As an example, a patient wearing a neuroprosthetic device (along with a body-external, portable processing device 100) comes to an eye specialist where a physician presents different stimuli to the patient and also records his pupil contraction. The stimuli and data relating to the pupil contractions are stored along with their recording delays and precise time stamps. The data can then be uploaded via an interface to the database 300 where it is synchronized with the brain activity of the patient acquired by the patient's neuroprosthetic device and sent to the database 300 via body-external, portable processing device 100. The patient's eye diagnostics can then be carried out by the physician as if having recorded the patient's brain activity in parallel by himself.

Another example relates to research data mining: Data streams from multiple patients can be processed, together with the data streams from other sensors, for new insights into the relations between neurological processes and these sensor data streams. Data sets can be exported, either in raw form or in preprocessed form (e.g., up- or down-sampled or converted in another file format).

For each type of data stream (e.g., neuronal data or electrocardiogram), the events represented by the data streams and the time stamps are stored in the database 300. For each device type, the parameters of the probability distribution for the delay are also stored in a product database 400.

For the sake of safe identification and security of data, a unique pseudonym may be assigned to each patient. In order to protect the private data of patients, each patient's personal data (e.g., name and address) is stored separately and encrypted together with its pseudonym. The patient's sensor data is stored unencrypted and associated only with the patient's pseudonym.

Access to the database 300 may be allowed only via encryption protocols that ensure privacy and ensure the authenticity of the person that wants to access the database.

The transmission of data via data transportation medium may be encrypted, whereas the strength of the encryption depends on the type of data that is transported and the transportation medium.

The security/encryption level is chosen by patient or her physician depending on the clinical need and the protection of privacy. Partial information maybe uploaded online continuously for clinical needs, for example critical safety parameters (heartrate etc.).

Figure 3:
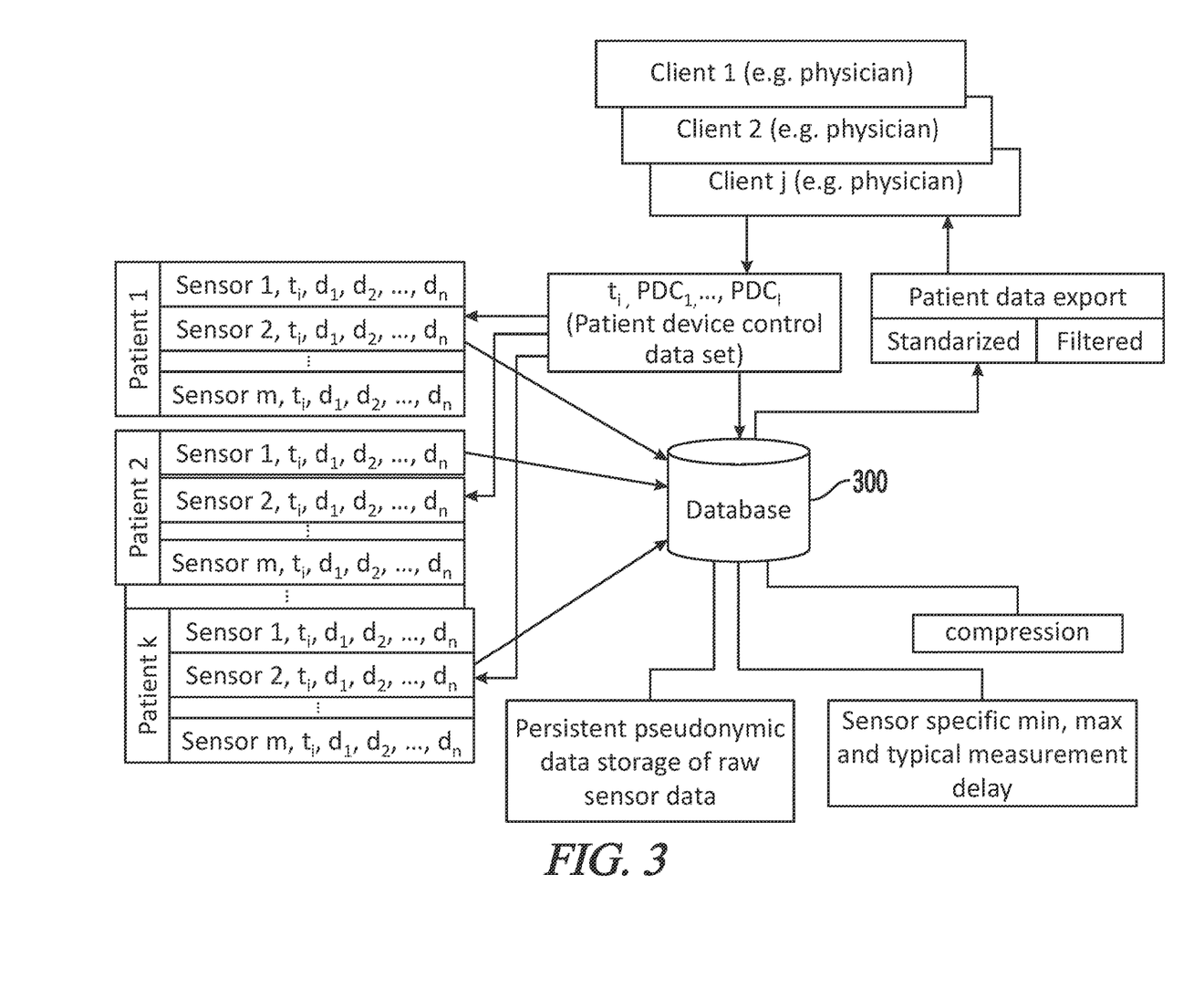
FIG. 3 is a scheme illustrating relation of time information and database content.

FIG. 3 is a scheme illustrating the relation of time information and database 300 content in a larger context. As can be seen from FIG. 3, the database 300 may store data streams from several patients 1, 2, . . . k. Each patient may be equipped with several sensor devices 1, 2 . . . , m, each sensor device sensing signals or parameters and producing data streams therefrom. As described before, each data stream $\{d_1, d_2, \ldots, d_n\}$ is representative of at least one event (represented by a signal). With each data stream $\{d_1, d_2, d_n\}$, a respective time stamp $t_i$ is associated. The time stamp $t_i$ (i being the index for the $i^{th}$ sensed event) is generated associated patient's body-external, portable processing device 100. Data streams along with their time stamps $t_i$ are transmitted from there to the database 300 (upon availability of a transfer medium 200) and stored there.

All or a number of the data streams $\{d_1, d_2, \ldots, d_n\}$ as well as control data for the sensors 10, 20-40, implant control unit 50, and actuators relating to one patient may be referred to as a patient data and device control data set (PDC). The data stored in database 300 may be exported in a standardized format and may be made available to clients 1, 2, . . . , j (e.g., physicians) for diagnosis. On the other hand, some clients may have direct access to particular or all PDC of the database 300. The data may be compressed for capacity or transmission reasons.

Sensor specific measurement delays $\Delta t_S$ of the sensor devices 10, 20-40, and delays $\Delta t_R$ of the recording means of processing device 100 may be accessed on a product specification database 400. This database 400 bay be external to the database 300 where the measurement data is stored. On the other hand, the delays $\Delta t_S$, $\Delta t_R$ pertinent to particular sensor devices 10, 20-40, and processing devices, respectively, may be kept available in database 300, too.

The database 300 may also store raw data, i.e., data as delivered by the sensors, which is not processed in any way.

The data collected by the processing device 100 can be used in several ways. First, the data can be pre-processed and then sent to the corresponding database 300 for further processing or analysis purposes as described above.

Second, the collected data can be transmitted to a stimulation unit, which is formed by implantable control unit 50 and stimulation implant, i.e., implantable electrode 10'. It may be connected via a real-time capable bus system (e.g., a CAN Bus) or via a wireless link with the processing device 100. The sensor data is sent to the stimulation device at the rate of its recording. The stimulation device comprises the controller unit 50 and the stimulation implant 10', whereby the controller is implemented by a control algorithm (e.g., neural network, fuzzy logic, etc.). The stimulation device comprises electrodes, signal generation, etc. The controller processes the sensor data according to its current parameter set, generates the corresponding set values for the actuator part of the system, and feeds the back to the actuator part of the system. In this way, a closed-loop stimulation system is provided.

All parts of the closed loop system (e.g., processing device, control algorithms) are configured using a vector of control parameters. Sensors may change their data acquisition rate or filter settings based on these parameters. Control algorithms are defined or adjusted by these parameters (e.g. edge weights in artificial neural networks, PID parameters, etc.).

Based on the analysis of measured data at the data base side (e.g. by a physician) the parameter vector can be updated via the transport medium 200. The parameter vector update can either be triggered by a poll request initialized by the measurement device or by a database-side push. The database push is triggered by inserting a new control set into the database 300.

As safety measure, the parameter space can be restricted to a safe subspace. The control vector is verified as to whether it is within the boundaries of the safe subspace before it is applied. Only if the vector is safe it is transferred to the corresponding device parts. The next measurement data will then be processed and generate control outputs according to the new parameter vector. Changes in the parameter vector are recorded along with the current time stamp t in the database 300. The safety subspace can be defined by the physician e.g. during an ambulatory treatment session.

The system architecture of the body-external, portable processing device 100 including the main software components is described in FIG. 3. All parts of the body-external, portable processing device 100 (including the plugin pipeline) store their data in the temporal storage 110. The processing is performed by a CPU. An operating system which is capable of running multiple threads is installed.

The system made up of multiple parts. One part is the configuration database 115, which is located preferably in the temporal storage (e.g., hard drive, flash drive, etc.) 110. This database 115 contains general application information including, what kinds of plugins (see below) need to be loaded, and what kinds of configuration parameters should be applied. Part of these parameters is the control vector as well as the possibly different safe parameter subspace for the patient and the physician.

The pipeline manager 130 uses the plugin pipeline builder 140 to create and initialize the plugin pipeline 150 based on the parameters in the configuration database 115. In addition, it controls start/stop of the measurement loop.

Figure 5:
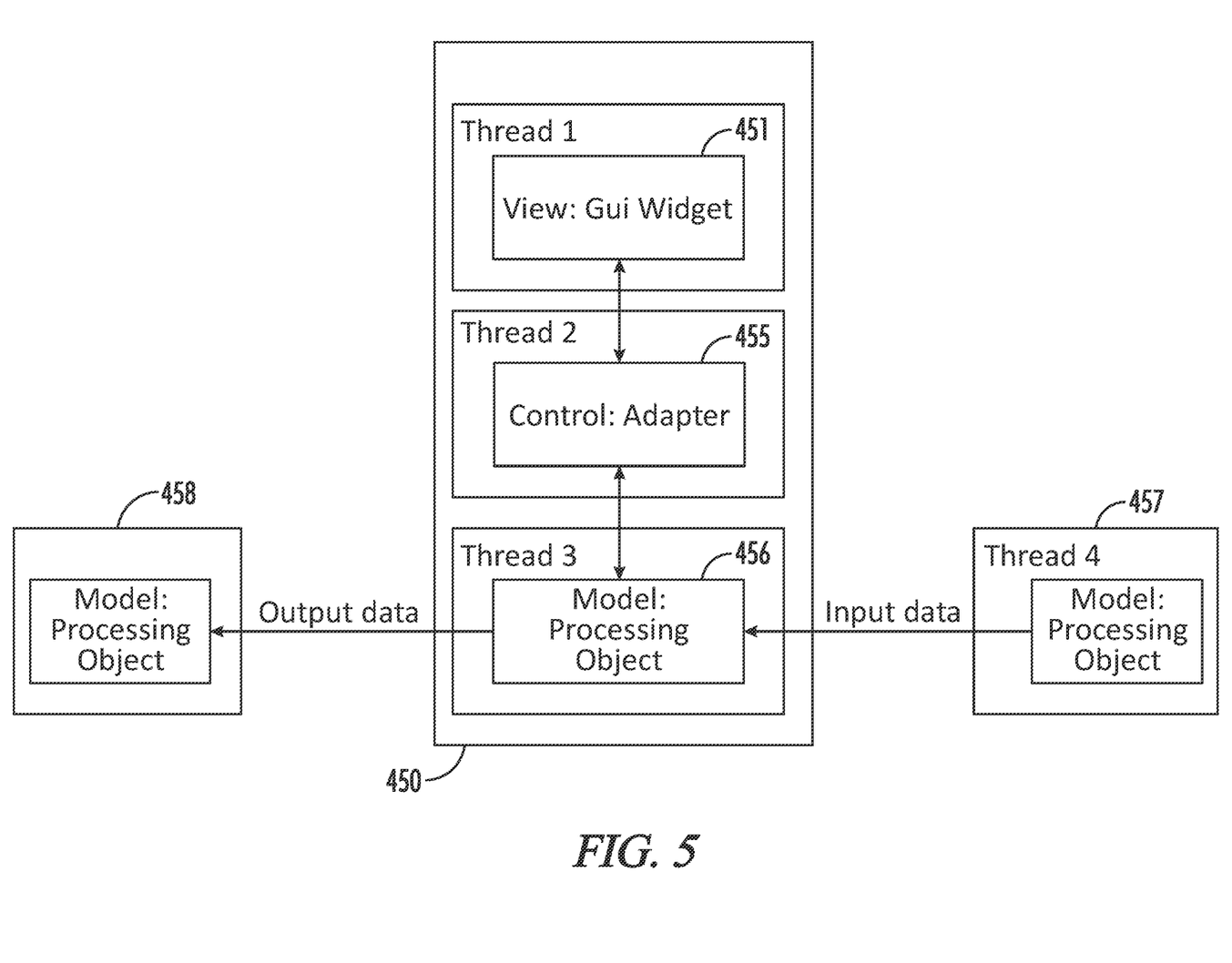
FIG. 5 is a model view of the control architecture of a single plugin.

The plugin pipeline 150 is made up of several plugins 450. FIG. 5 is a block diagram of a single plugin. The individual plugins are designed by the model view control software design pattern. Therefore, the graphical user interface (GUI) of each plugin 450 may only access the model via the controller (i.e. adapter) 455. The adapter 455 modifies the model (i.e. processing object) 456, which in turn tells the adapter 455 about model changes. These changes are then sent back to the view 451. Therefore, the system's main GUI consists of a view container containing the individual plugins' views. New data is pushed to the processing object by its predecessor, locally processed and then passed to the successor. Lazy copying is applied. Therefore, the data is only copied if the data needs to be changed. Every plugin part is running in its own thread. Processing objects 456, 457, 458 can be connected if the type of the data of two consecutive objects is of the same type. A connection graph is stored as part of the configuration database 115. The connection graph represents the plugins and their interconnections, wherein the nodes of the graph correspond to the plugins, and edges of the graph correspond to the connections between the plugins. Thus, based on this graph the individual plugins are connected to each other for implementing a particular hardware/software system on the body-external, portable processing device 100.

Figure 4:
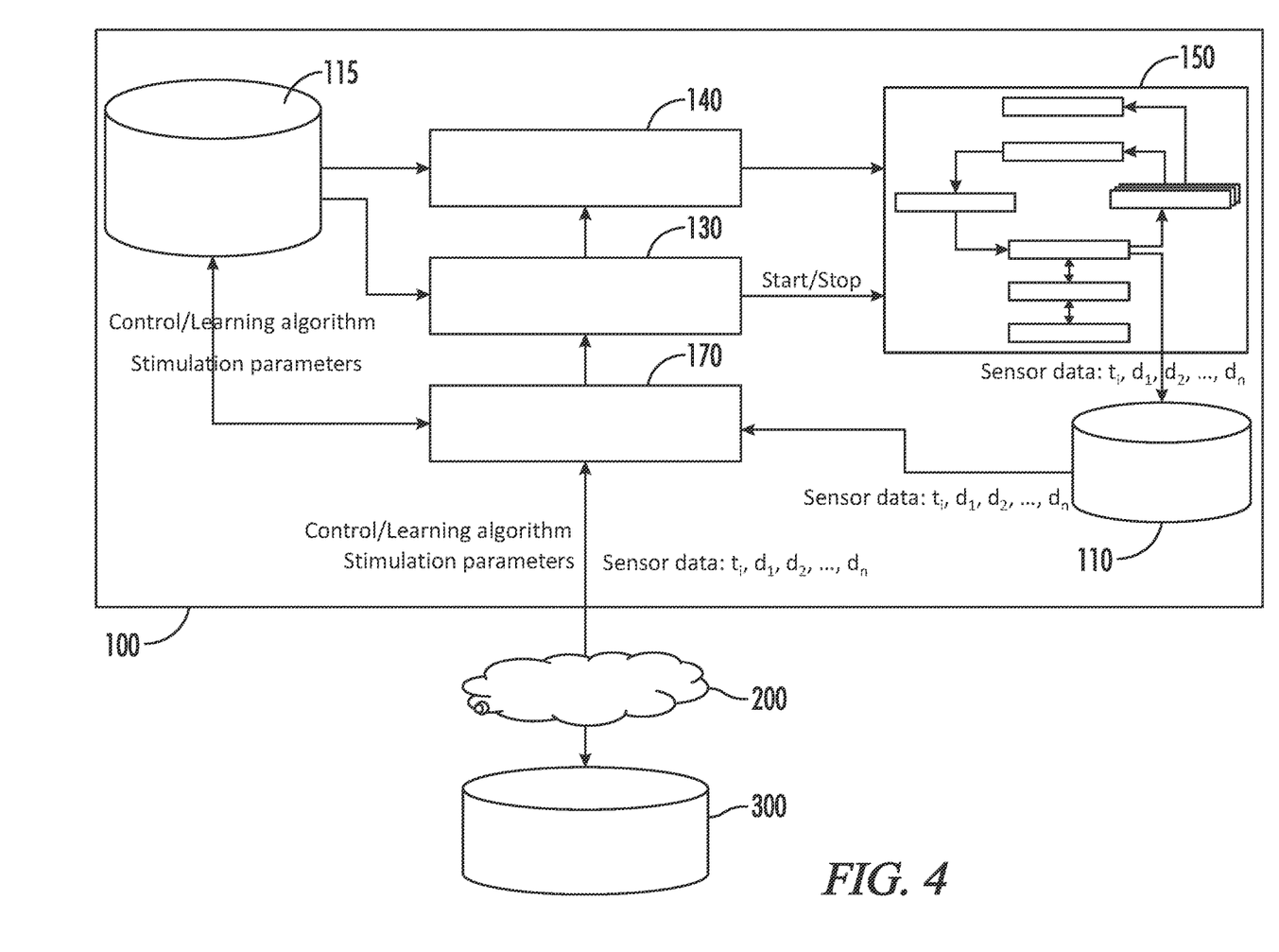
FIG. 4 is a scheme of the device system architecture with central database connection.
Figure 6:
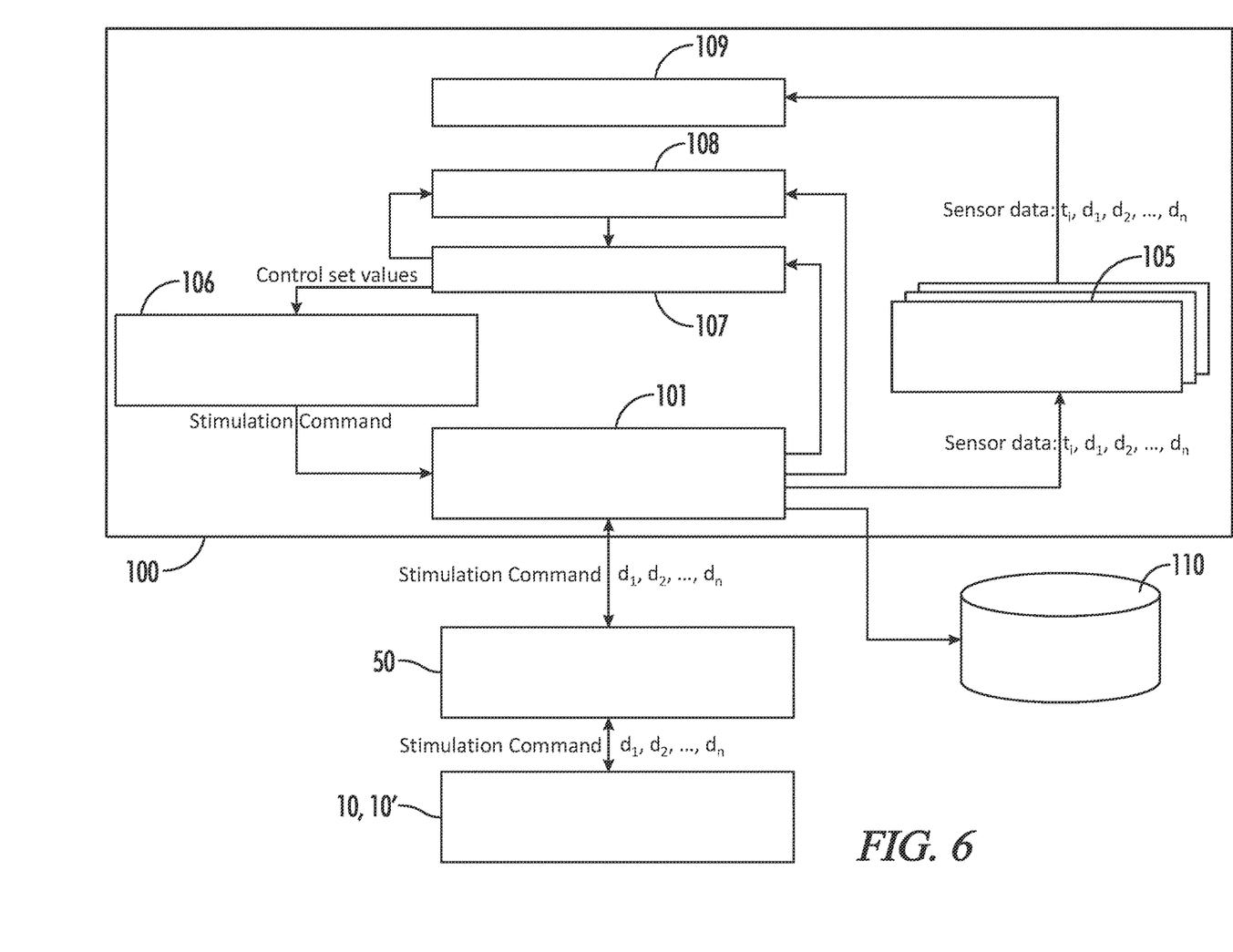
FIG. 6 is a view on the plugin pipeline for closed-loop applications.

The flexible and scalable plugin system can be configured such that a closed-loop system is formed (see FIG. 6). There is one hardware communication plugin 101 for every sensor 10, 20-40 connected to the system. For example, FIG. 4 illustrates the connection to a neural implant 10 for neural signals. Stimulation commands $\{d_1, d_2, \ldots, d_n\}$ are passed by the plugin to the implant control unit 50, which is connected to the body-external, portable processing device 100. The implant control unit 50 in turn is connected to neural implant 10. The neural signal recordings are sent via the implant control unit 50 back to the hardware communication plugin 101.

This sensor data is sent to four different locations. First, it is extended by its time stamp t and stored to the temporal storage 110. This temporal storage 110 is preferably (but not necessarily) located on the same persistent drive as the configuration database 115. For visualization the sensor data is processed by possibly multiple preprocessing plugins 105 (e.g. notch filters, etc.). The result of this processing is sent to a visualization plugin 109, which plots the current sensor readings. The sensor data from the hardware communication plugin 101 can also be sent to a control algorithm plugin 107 and to the parameter learning algorithm plugin 108.

The purpose of the control algorithm plugin 107 is to generate stimulation set values, which correspond to the data read. The control set is influenced by the current control parameter vector, which may vary depending on the control algorithm in use.

The optional parameter learning algorithm plugin 108 starts with the control parameter set provided in the configuration database 115. Then, based on the sensor data and the output of the control algorithm plugin 107 it generates modifications of the control parameters if necessary. Both the control algorithm plugin as well as the learning algorithm may locally store several sensor readings in order to provide the means of an integrated mechanism for control.

The stimulation generator plugin 106 generates stimulation commands from the set values and sends them to back to the hardware communication plugin 101, which closes the control loop. It should be noted that there may be more than one kind of sensor 10 involved, which may all sent their data to either one or multiple control/learn algorithm pairs (cascade control).

The communication manager 170 (refer to FIG. 6) connects the temporal storage 110 through the transport medium 200 with a central database 300 if the connection is available and intended. The communication manager 170 ensures that all sensor data collected since the last synchronization is transferred to the central database 300. In turn, it pulls any configuration updates to the body-external, portable processing device 100. The configuration updates (e.g. control/learning algorithm, control parameter vectors, etc.) is first evaluated for correctness and safety. If the data is sound it is stored into the configuration database 115, and the pipeline manager is informed about these updates. The pipeline manager performs the required pipeline changes (e.g. replace control and learning algorithm, change control parameter vector).

As an example, cross-correlation of sensor activity and recording after stimulation or other measures of effectiveness can be used to determine optimal weights for each sensor of the closed-loop algorithm.

As a further example, the body-external, portable processing device 100 itself may run online or offline learning algorithms for adjusting the stimulation parameters. This is achieved by providing each sensor data stream and control algorithm output continuously as input of the learning algorithm. The output can change control parameters "on the fly" (e.g., applied to a fuzzy logic controller with an artificial neural network for online control parameter learning). The advantage of this online learning approach is that it can handle daily fluctuations of the patient's condition.

Another example is to record environment for safety or adaptation of stimulation parameters with respect to safety, for example to increase stimulation to a more effective level when driving a car. Hereto, a determination is needed whether the person is actually driving a car. This may be done by combining a GPS sensor, and an body-external, portable movement sensor which detects movements of e.g., the hands or arms of the person. Thus, if the GPS sensor detects a movement with a higher speed, and the body-external, portable movement sensor detects movements according to a typical driver's profile, the system may increase (or suggest to the person increasing) the strength and/or frequency of the stimulation pulses.

Moreover, the exactly time-tagged data streams may be used for calibrating the system, by recording the system's impulse response, which is approximated by recording the neural activities/sensor activities in response to the strongest possible single pulse stimulation/actuator activity applied. As the stimulation pulse for safety reasons is limited in strength to the maximal stimulation (voltage or current) allowed, this characterization is carried out repeatedly, typically 10-25 times, and the results are averaged until only minor differences occur and statistical significance of the model is reached.

The model of the system generated by this characterization then can be used to predict sensor activities in response to certain stimulation or actuator patterns. This can be used twofold: On the one hand, to define the stimulation/actuator activities that produce sensor activity(ies) indicative for a desired patient state, for example low oscillations in the beta-range in certain brain regions, i.e., the motor cortex or in the nucleus subthalamicus. And on the other hand, to prevent stimulation parameters that achieve undesired neural activities or brain states, for example activity that leads to increased oscillations in the beta range in certain brain regions, activity that might lead to seizures, invoke uncontrolled movements.

The data streams may be stored in the data base 300 in different ways. For each patient, the data streams relating to different parameter may be stored in a two-dimensional matrix:

time×parameters, separate for each patient.

For several patients, in particular if the data streams of several patients correspond to each other, the data streams may be stored in three-dimensional matrix:

time×parameters×patient.

The delays (between the sensing the signal relating to an event by the sensor device 10, 20-40 and the recording of the signal by the processing device 100, often a few hundred ms) may be subtracted before alignment in the database 300. This subtraction may either occur upon storage in the temporary processing device 100 or upon storage at the database 300. Of course, if diagnosis and/or adaptation of parameters is done at a later time, the alignment may be done only at that later occasion.

The embodiments disclosed further comprise:

A brain stimulation method, wherein neuronal signals of a patient are continuously sensed by at least one sensor device (and based on the sensed signals, stimulation signals are applied to the patient by at least one stimulation device,
wherein the sensed signals are transmitted to a body-external, portable processing device wherein the sensed signals are evaluated, and based on the evaluated signals, stimulation control signals are generated and transmitted to the stimulation device where based on the stimulation control signals the stimulation signals are generated.

According to a further embodiment, at least one parameter relating to a physical condition of the patient is sensed by at least one further sensor device, and transmitted to and evaluated by the body-external, portable processing device when generating the stimulation control signals.

According to a further embodiment, the stimulation control signals are generated on the basis of a plurality of signals sensed during a predetermined time span, the plurality of signals being stored in the body-external, portable processing device.

According to a further embodiment, preferably in real-time, the following steps are performed:
the sensed signals are continuously transmitted to the body-external, portable processing device, wherein the sensed signals are continuously evaluated, and based on the evaluated signals, the stimulation control signals are continuously generated and continuously fed back to the stimulation device.

Further provided is method of calibrating a brain stimulation system, the system being adapted for performing the inventive method as described above,
wherein a stimulation signal is generated and applied to the patient,
wherein the stimulation signal is a single impulsion of maximal strength, and the sensed signals are recorded.

According to a further embodiment of the inventive calibration method, the sensed signals are associated with time stamp information, the time stamp information being representative of the point in time when the signals are sensed.

According to a further embodiment of the inventive calibration method, adaptation of the brain to the stimulation signals is determined by the body-external, portable processing device based on the signals received from the least one sensor device, and upon determination of the adaptation, the stimulation control signals are modified.

According to a further embodiment of the inventive calibration method, the stimulation control signals are generated by the body-external, portable processing device as a predetermined function of the signals sensed by the at least on sensor device, whereby the function is adapted over time, preferably by changing weighting factors of the signals sensed by the at least on sensor device and/or by modifying the functional relationship of the signal sensed by the at least on sensor device.

Yet further according to the embodiments provided is a computer-readable storage medium comprising program code for performing the method as described above, when loaded into a computer system.

The invention claimed is:

1. A computer-implemented method for controlling a brain stimulation system, the brain stimulation system comprising:
an implantable sensor device which is adapted for being placed into a brain cavity of a patient,
a neural stimulation device which is adapted for being placed into the brain cavity, and for applying stimulation signals to the patient, the neural stimulation device being a neural implant,
a body-external, portable processing unit, the method comprising the following steps:
receiving, by the body-external, portable processing unit, a number of data streams, at least one data stream thereof being representative of at least one physiologic signal of a patient sensed by the sensor device, the physiologic signal representing an electrical brain activity,
generating at least one time stamp information at the body-external, portable processing unit, the at least one time stamp information being based on a time reference comprised by the body-external, portable processing unit, each time stamp information being associated with a respective data stream of the number of data streams,
each time stamp information being representative of the point in time of associating the time stamp information with the respective data stream, recording, in a body-external temporal storage device, the at least one data stream and at least one time stamp information associated thereto, and
associating a respective time shift information with each time stamp information, and recording the time shift information associated with the time stamp information in the body-external temporal storage device, the time shift information being at least partially based on the corresponding sensor device associated with the corresponding data stream, and representative of a delay between a point in time of sensing the at least one signal by the sensor device and the point in time of associating the time stamp information with the data stream representative of the at least one signal, and
updating therapeutic parameters of the neural implant based on the at least one data stream thus temporally aligned, and sending the therapeutic parameters to the stimulation device,
wherein the time shift information is additionally representative of a delay between the point in time of associating the time stamp information and a point in time of recording the data stream by the body-external, portable processing device.

2. The method of claim 1, further comprising transmitting the recorded at least one data stream, and the respective time stamp information to a database, and storing the at least one data stream, the time stamp information, and the associated time shift information in the database.

3. The method of claim 1, wherein at least one data stream of the number of data streams is representative of at least one patient's body-external signal sensed by a predetermined sensor device.

4. The method of claim 3, wherein transmitting to and storing in the database is done when a data transmission medium is available to the body-external, portable processing device.

5. The method of claim 1, wherein the time stamp information is generated using a time reference which delivers Coordinated Universal Time information, in particular one of a radio-controlled clock, a time server, a wide area network time, local area network time, mobile communication network, and a Global Positioning Service device.

6. The method of claim 1, wherein at least one physiologic signal represents at least one value of a parameter, the parameter being one of pH, blood glucose, EMG, heart rate, skin conductivity, body movement, blood pressure, geolocal position, temperature, lightening level, concentrations of biomolecules, noise, and sound.

7. The method of claim 1, wherein at least one data stream is sensed by at least one body-external sensor device.

8. The method of claim 1, wherein the recorded at least one data stream, the time stamp information, and the associated time shift information relate to a neuroprosthetic device of the patient, and are used for adaptation of at least one parameter of a neuroprosthetic device of the patient,
the adaptation being performed in a patient's body-external computer system, and the at least one parameter is transmitted to the neuroprosthetic device via a predetermined communication channel, in particular via a data transmission medium.

9. A non-transitory computer-readable storage medium comprising program code, the program code containing instructions for performing the method according to claim 1, when loaded into a computer system.

10. A computer-implemented method for controlling a brain stimulation system, the brain stimulation system comprising:
an implantable sensor device which is adapted for being placed into a brain cavity of a patient,
a neural stimulation device which is adapted for being placed into the brain cavity, and for applying stimulation signals to the patient, the neural stimulation device being a neural implant,
a body-external, portable processing unit, the method comprising the following steps:
receiving, by the body-external, portable processing unit, a number of data streams, at least one data stream thereof being representative of at least one physiologic signal of a patient sensed by the sensor device, the physiologic signal representing an electrical brain activity,
generating at least one time stamp information at the body-external, portable processing unit, the at least one time stamp information being based on a time reference comprised by the body-external, portable processing unit, each time stamp information being associated with a respective data stream of the number of data streams,
each time stamp information being representative of the point in time of associating the time stamp information with the respective data stream, recording, in a body-external temporal storage device, the at least one data stream and at least one time stamp information associated thereto, and
associating a respective time shift information with each time stamp information, and recording the time shift information associated with the time stamp information in the body-external temporal storage device, the time shift information being at least partially based on the corresponding sensor device associated with the corresponding data stream, and representative of a delay between a point in time of sensing the at least one signal by the sensor device and the point in time of associating the time stamp information with the data stream representative of the at least one signal, and
updating therapeutic parameters of the neural implant based on the at least one data stream thus temporally aligned, and sending the therapeutic parameters to the stimulation device,
wherein the delay is derived from a predetermined probability distribution of delays between the actual happening of the event and the time when the time stamp is recorded.

11. A computer-implemented method for controlling a brain stimulation system, the brain stimulation system comprising:
an implantable sensor device which is adapted for being placed into a brain cavity of a patient,
a neural stimulation device which is adapted for being placed into the brain cavity, and for applying stimulation signals to the patient, the neural stimulation device being a neural implant,
a body-external, portable processing unit, the method comprising the following steps:
receiving, by the body-external, portable processing unit, a number of data streams, at least one data stream thereof being representative of at least one physiologic signal of a patient sensed by the sensor device, the physiologic signal representing an electrical brain activity,
generating at least one time stamp information at the body-external, portable processing unit, the at least one time stamp information being based on a time reference comprised by the body-external, portable processing unit, each time stamp information being associated with a respective data stream of the number of data streams,
each time stamp information being representative of the point in time of associating the time stamp information with the respective data stream, recording, in a body-external temporal storage device, the at least one data stream and at least one time stamp information associated thereto, and
associating a respective time shift information with each time stamp information, and recording the time shift information associated with the time stamp information in the body-external temporal storage device, the time shift information being at least partially based on the corresponding sensor device associated with the corresponding data stream, and representative of a delay between a point in time of sensing the at least one signal by the sensor device and the point in time of associating the time stamp information with the data stream representative of the at least one signal, and
updating therapeutic parameters of the neural implant based on the at least one data stream thus temporally aligned, and sending the therapeutic parameters to the stimulation device,
wherein the transmitted data streams are encrypted.

* * * * *